United States Patent [19]

Chu et al.

[11] Patent Number: 5,084,445
[45] Date of Patent: Jan. 28, 1992

[54] 3'-AZIDO-2',3'-DIDEOXY-5-METHYLCYTIDINE

[75] Inventors: Chung K. Chu, Athens; Raymond F. Schinazi, Decatur, both of Ga.

[73] Assignees: University of Georgia Research Foundation, Inc., Athens; Emory University, Atlanta, both of Ga.

[21] Appl. No.: 362,756

[22] Filed: Jun. 7, 1989

Related U.S. Application Data

[63] Continuation-in-part of Ser. No. 159,246, Feb. 23, 1988, abandoned, which is a continuation-in-part of Ser. No. 16,136, Feb. 18, 1987, Pat. No. 4,841,039, which is a continuation of Ser. No. 857,947, May 1, 1986, Pat. No. 4,681,933, and a continuation of Ser. No. 104,438, Oct. 2, 1987, Pat. No. 4,916,122, which is a continuation-in-part of Ser. No. 7,473, Jan. 28, 1987, abandoned.

[51] Int. Cl.$^5$ ........................ A61K 31/70; A61K 37/22
[52] U.S. Cl. ........................................ 514/49; 514/51; 424/450
[58] Field of Search ................ 514/46, 49, 50, 51; 424/450

[56] References Cited

U.S. PATENT DOCUMENTS

| 3,282,921 | 11/1968 | Verheyden et al. | 536/23 |
|---|---|---|---|
| 3,687,931 | 8/1972 | Verheyden et al. | 536/23 |
| 3,755,295 | 8/1973 | Verhdyden et al. | 536/23 |
| 3,775,397 | 11/1973 | Etzold et al. | 536/23 |
| 3,817,982 | 6/1974 | Verheyden et al. | 536/23 |
| 4,071,680 | 1/1978 | Cook | 536/23 |
| 4,093,715 | 6/1978 | Lin et al. | 514/50 |
| 4,093,716 | 6/1978 | Lin et al. | 514/50 |
| 4,128,639 | 12/1978 | Lin et al. | 514/50 |
| 4,210,638 | 7/1980 | Greer | 514/49 |
| 4,230,689 | 10/1980 | Bobek et al. | 424/74 |
| 4,331,662 | 5/1982 | Eckstein et al. | 514/50 |
| 4,522,811 | 6/1985 | Eppstein et al. | 514/2 |
| 4,540,566 | 9/1985 | Davis et al. | 424/22 |
| 4,604,382 | 8/1986 | Lin et al. | 514/49 |
| 4,710,492 | 12/1987 | Lin et al. | 514/50 |
| 4,724,232 | 2/1988 | Rideout et al. | 514/50 |
| 4,780,453 | 10/1988 | Rideout et al. | 514/50 |
| 4,788,181 | 11/1988 | Driscoll et al. | 514/49 |
| 4,916,122 | 4/1990 | Chu et al. | 514/50 |

FOREIGN PATENT DOCUMENTS

| 86301897.4 | 1/1986 | European Pat. Off. |
| 0217580 | 4/1987 | European Pat. Off. |
| 8637071.0 | 4/1987 | European Pat. Off. |
| 88103543.0 | 10/1988 | European Pat. Off. |
| 88303248.4 | 10/1988 | European Pat. Off. |
| 2244490A1 | 7/1985 | Fed. Rep. of Germany |
| 3608606A1 | 9/1986 | Fed. Rep. of Germany |
| 81007177 | 1/1981 | Netherlands |

OTHER PUBLICATIONS

Lin et al., J. Med. Chem., 26: 1691–1696, 1983.
Sandstrom et al., Drugs, 34: 372–389, 1987.
(List continued on next page.)

Primary Examiner—John W. Rollins
Attorney, Agent, or Firm—Kilpatrick & Cody

[57] ABSTRACT

The present invention is an antiviral composition which includes a means and method for delivering an HIV-inhibitory amount of an active compound of the general formula:

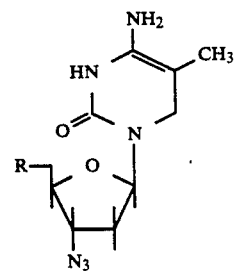

wherein R is OH, monophosphate, diphosphate, or triphosphate, or a pharmacologically acceptable salt thereof; and wherein the means is a pharmaceutically acceptable carrier. In the preferred embodiment, an effective dose of 3'-azido-2',3'-dideoxy-5-methylcytidine, or its derivatives is administered in a pharmaceutically acceptable carrier to a patient for the treatment of AIDS.

15 Claims, 1 Drawing Sheet

OTHER PUBLICATIONS

Mitsuga et al., *J. Sci. Soc.*, pp. 277–288, 1985.
Herdewijn et al., *J. Med. Chem.* 30, 1270 (1987).
Herdewijn et al., *J. Med. Chem.* 31, 2040 (1988).
Lin et al., *J. Med Chem.* 30, 440 (1987).
Lin et al., *J. Med. Chem.* 26, 1691 (1983).
Alarcon et al., *Antimicrob. Agents and Chemother.* 32(8), 1257 (1988).
Alcina et al., *Antimicrob. Agents and Chemother.* 32(9), 1412 (1988).
Anzai et al., *Agr. Biol. Chem.* 37(2), 345 (1973).
Balzarini et al., *Mol. Pharmacol.*, 32, 162 (1987).
Brubaker et al., *Chem. Abstr.* 102:226110x (1985).
Busson et al., *Nucleic Acids Symp. Ser.* 9, 49–52 (1981) (*Chem. Abstr.* 96:69346s (1982)).
Camarasa et al., *J. Med. Chem.* 28, 40 (1985).
Chu et al., *J. Med. Chem.* 21(1), 96 (1978).
Classon et al., *Acta Chemica Scandinavica* B36, 251 (1982).
Colla et al., *Eur. J. Med. Chem.—Chim. Ther.* 20(4), 295 (1985).
DeClercq, *Meth and Find Exptl Clin Pharmacol* 2(5), 253–267 (1980).
DeClercq et al., *Pharm.* (*Chem. Abstr.* 97:174446t (1982)).
DeClercq, *Curr. Chemother. Immunother., Proc. Int. Congr. Chemother.*, 12th 1981 1062 (1982) (*Chem. Abstr.* 97:174446t (1982)).
Dyatkina et al., *Bioorg. Khim.* 12(2), 408 (1986) (*Chem. Abstr.* 105:227205f (1986)).
Dyatkina et al., *Biiorg. Khim.* 9, 132 (1983).
Fox et al., *Herpes Viruses and Virus Chemotherapy* Elsevier Science Publishers B.V. (Biomedical Division) 53–56 (1985).
Furman et al., *Proc. Natl Acad. Sci., USA* 83, 8333 (1986).
Krentisky et al., *J. Med. Chem.* 26(6), 891 (1983).
Lin et al., *Biochem. Pharmacol.* 36, 2713 (1987).
Lin et al., *J. Med. Chem.* 26, 544 (1983).
Lin et al., *J. Med. Chem.* 21(1), 109 (1978).
Lin et al., *Biochem. Pharmacol.* 36, 311 (1987).
Mitsuya et al., *Proc. Natl. Acad. Sci. USA* 82, 7096 (1985).
Mitsuya and Broder, *Proc. Natl. Acad. Sci. USA* 83, 1911 (1986).
Roseman et al., *J. Am. Chem. Soc.* 83, 659 (1961).
Schinazi et al., *Antimicrob. Agents and Chemother.* 22(3), 499 (1982).
Schinazi et al., *Antimicrob. Agents and Chemother.* 28(4), 552–560 (1982).
Schinazi et al., *Antimicrob. Agents and Chemother. 30(3), 491 (1986).*
Schinazi et al., *Antimicrob. Agents and Chemother.* 32(12), 1784 (1988).
Schinazi et al., *J. Cellular Biochemistry* P405, 74 (1987).
Schinazi et al., Anti–Human Immunodeficiency Virus (HIV-1) Activity of 3'-Azido-2',3'-Dideoxyuridine in Different Cell Lines".
Shealy et al., *J. Heterocyclic Chemistry* 13(5), 1015 (1976).
Verheyden et al., *Chem. Abstr.* 81:63942b (1974).
Zaitseva et al., *Bioorg. Khim.* 10(5), 670 (1984) (*Chem. Abstr.* 101:192378c (1984)).
Broder, Modern Concepts and Therapeutic Challenges, *AIDS*, p. 303, Marcel Dekker, Inc., New York 1987.
DeClercq, *J. Med. Chem.* 29(9), 1561 (1986).
Fischl et al., *New England Journal of Medicine* 317(4), 192 (1987).
Mitsuya et al., Nature, 325, 773 (1987).
Yarchoan et al., *New England Journal of Medicine* 316, 557 (1987).
Chu et al., *J. Med. Chem.*, vol. 32, No. 3, pp. 612–617, Mar. 1989.
Herdewijn, P., et al., *J. Med. Chem.*, vol. 31, No. 10, Oct. 1988.
Lin, T.-S., et al., *J. Med. Chem.*, vol. 31, No. 2, Feb. 1988.
Galegov, G. A., et al., *Mol. Biol.*, vol. 22, No. 3, 1988.
Dyatkina, N. B., et al., *Bioorg. Khim.*, vol. 12, No. 8, 1986.

3'-AZIDO-2',3'-DIDEOXY-5-METHYLCYTIDINE

The U.S. Government has rights in this invention arising out of a Veterans Administration Merit Review Award.

This is a Continuation-in-Part of U.S. Ser. No. 159,246 entitled "2,3'-Dideoxynucleosides as Anti-Retroviral Compositions and Their Method of Preparation", filed Feb. 23, 1988, now abandoned which is a Continuation-in-Part of (1) U.S. patent application Ser. No. 016,136 entitled "2,3'-Dideoxy-5-Substituted Uridines and Related Compounds as Antiviral Agents" filed Feb. 18, 1987 by Chung K. Chu and Raymond F. Schinazi, now U.S. Pat. No. 4,841,639, which is a continuation of U.S. Ser. No. 857,947 filed May 1, 1986 by Chung K. Chu and Raymond F. Schinazi, now U.S. Pat. No. 4,681,933, and (2) U.S. patent application Ser. No. 104,438 filed Oct. 2, 1987 entitled "3'-Azido-2',3'-Dideoxyuridine Antivira Composition" by Chung K. Chu and Raymond F. Schinazi, now U.S. Pat. No. 4,916,122, which is a continuation in part of U.S. Ser. No. 007,473 filed Jan. 28, 1987 entitled "3'-Azido-2',3'-Dideoxypyrimidines and Related Compounds as Antiviral Agents", now abandoned.

BACKGROUND OF THE INVENTION

The present invention is in the field of pharmaceutical delivery systems, and in particular relates to the use of 3'-azido-2',3'-dideoxy-5-methylcytidine and compositions thereof for the inhibition of viral infections.

AIDS was recognized as early as 1979. The number of cases reported to the Centers for Disease Control (CDC) has increased dramatically each year since then, and in 1982 the CDC declared AIDS a new epidemic. AIDS is generally accepted at this time to be a consequence of infection with the retrovirus, human immunodeficiency virus (HIV-1). Antibodies to these viruses are present in over 80% of patients diagnosed as having AIDS or pre-AIDS syndrome, and have been found with high frequency in identified risk groups.

A patient is generally diagnosed as having AIDS when a previously healthy person with an intact immune system acquires impaired T-cell immunity. The impaired immunity usually appears over a period of eighteen months to three years. As a result of this impaired immunity, the patient becomes susceptible to opportunistic infections, various types of cancer such as Kaposi's sarcoma, and other disorders associated with reduced functioning of the immune system.

Another condition associated with the presence of anti-HIV antibodies is AIDS-related complex, or ARC. This condition is thought to lead eventually to AIDS.

A number of compounds have been found to have antiviral activity against this virus, including HPA-23, interferons, ribavirin, phosphonoformate, ansamycin, suramin, imuthiol, penicillamine, rifabutin, AL-721, 3'-azido-3'-deoxythymidine (AZT), and other 2,'3'-dideoxynucleosides, such as 2',3'-dideoxycytidine (DDC), 2',3'-dideoxyadenosine (DDA), 3'-azido-2',3'-dideoxyuridine (AzddU), 2',3'-didehydrocytidine, 3'-deoxy- 2',3'-didehydrothymidine and 3'-azido-5-ethyl-2',3'-dideoxyuridine (AzddEU). The present application is a continuation-in-part of applications directed to both AzddEU and AzddU.

In general, inhibitors of cellular processes will often limit viral replication, but such agents are usually quite toxic for the host as well. Most of the antiviral drugs that have been discovered so far cannot be prescribed for a prolonged period of time because of their toxicity. For example, a compound structurally related to the compounds of the present invention, idoxuridine, is limited in clinical usefulness to topical application in ophthalmic solutions for treatment of herpetic keratitis because of its toxicity to normal cells.

AZT has been studied extensively in humans for treatment of HIV-1 infections. AZT can decrease the frequency of opportunistic infections in a selected group of individuals with acquired immunodeficiency syndrome (AIDS) or AIDS-related complex (ARC). However, bone marrow toxicity and other side effects may limit its usefulness. For example, Richman et al. has shown that because of AZT-associated hematological abnormalities, twenty-one percent of patients undergoing AZT therapy required multiple blood transfusions during the six month treatment period. Bone marrow depression may be due to the accumulation of phosphorylated AZT within cells, which may result in a substantial depression of thymidine 5'-triphosphate pools. Another drawback of AZT is its short half life in humans (about 1.1 hour) and its elimination in urine as 3'-azido-3'-deoxy-5'-gluronylthymidine, a metabolite with no substantial antiviral activity.

In light of the state of the art, it is clear that there remains a strong need for new effective antiviral agents, especially those with low toxicity to normal cells. More particularly, in light of the lack of an effective treatment for AIDS and the fact that AIDS patients require a long term therapy, possibly for an entire life span, there remains a great need for development of new antiviral agents of low toxicity for AIDS treatment.

It is therefore an object of the present invention to provide a new antiviral composition that has low toxicity toward uninfected cells.

It is a further object of this invention to provide a composition for inhibiting the replication of HIV-1 and other retroviruses.

It is yet another object of the present invention to provide a method for the prevention and treatment of infection by HIV-1 and other retroviruses.

SUMMARY OF THE INVENTION

The present invention is an antiviral composition which includes a means for delivering an HIV-inhibitory amount of an active compound of the general formula:

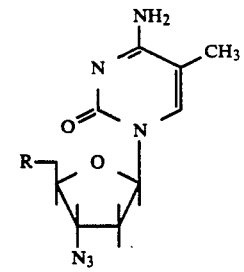

wherein R is OH, monophosphate, diphosphate, or triphosphate, or a pharmacologically acceptable salt thereof; and wherein the means is a pharmaceutically acceptable carrier. Another aspect of the present invention is a method of treating viral diseases which includes administering an effective dose of 3'-azido-2',3'- dideoxy-5-methylcytidine in a pharmaceutically acceptable carrier.

A primary advantage of this composition is its highly selective anti-retroviral activity, in combination with low cytotoxicity. The compound is not active against herpes simplex virus type 1 or coxsackievirus B4, and is only weakly active against Friend murine retrovirus. Most importantly, it exhibits no toxicity to erythroid precursor cells when tested up to 100μM.

In the preferred embodiment, the compound of the present invention is provided as an active ingredient in compositions delivering an effective amount of compound to inhibit HIV when administered to a patient. The effective amount is extrapolated from the concentration inhibiting viral replication in vitro without significant damage to host cells.

In another embodiment, a composition delivering an effective amount of 3'-azido-2',3'-dideoxy-5-methylcytidine or its derivative is used in vitro in solution or in cell culture to inhibit HIV.

DETAILED DESCRIPTION OF THE INVENTION

Figure 1:
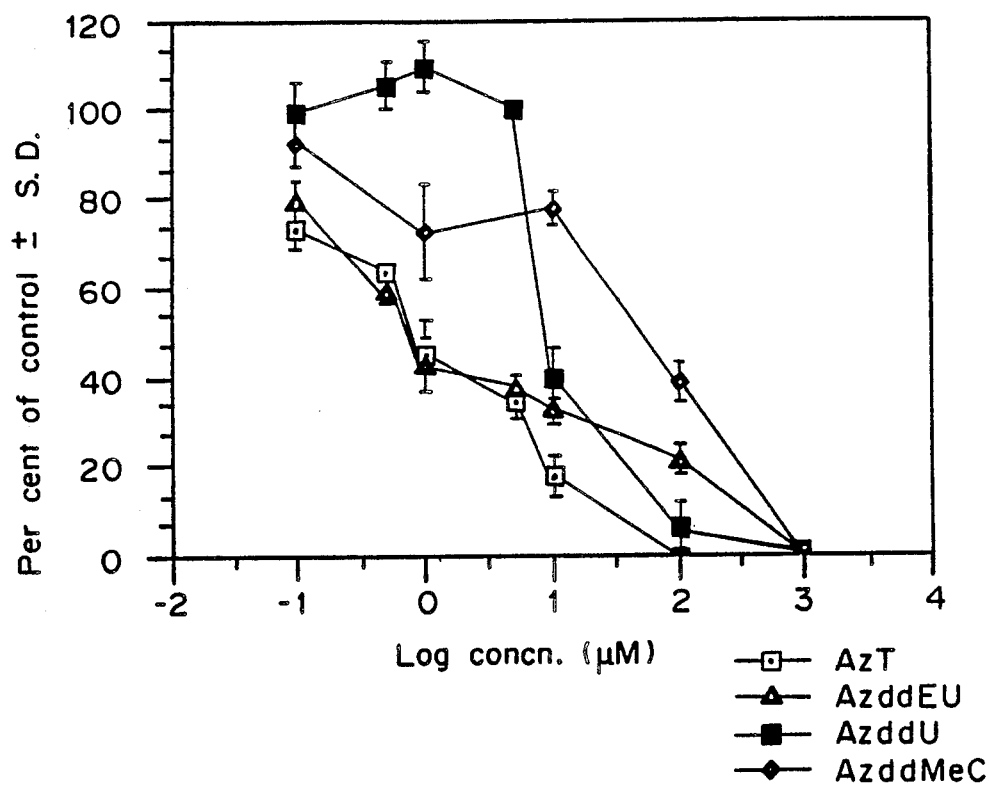
FIG. 1 is a graph showing the relative effect of 3'-azido-3'-deoxythymidine (AZT), 3'-azido-2',3'-dideoxyuridine (AzddU), 3'-azido-5-ethyl-2',3'-dideoxyuridine (AzddEU) and 3'-dideoxy-2',3'-dideoxy-5-methylcytidine (AzddMeC) on colony formation of human granulocytes-macrophage precursor cells.

The present invention is a pharmaceutical delivery system which delivers an HIV-inhibitory amount of 3'-azido-2',3'-dideoxy-5-methylcytidine, which has the general formula:

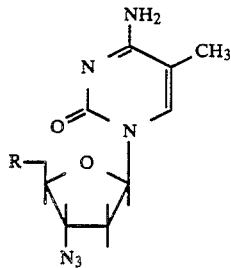

wherein R is OH, monophosphate, diphosphate, or triphosphate, and pharmacologically acceptable salts thereof; wherein the means is a pharmaceutically acceptable carrier.

Another aspect of the present invention is a method of treating viral diseases which includes administering an effective dose of 3'-azido-2',3'-dideoxy-5-methylcytidine in a pharmaceutically acceptable carrier.

The present invention is based on the discovery that 3'-azido-2',3'-dideoxy-5-methylcytidine (AzddMeC) and phosphorylated derivatives thereof exert a highly selective activity against certain viruses, in particular against the HIV retrovirus, while, at the same time, exhibiting very low toxicity towards normal, uninfected, cells.

3,-Azido-2',3'-dideoxy-5-methylcytidine is a known compound. See, for example, Lin, et al., J. Med. Chem. 26, 1691-1696 (1983). Lin, et al. tested the activity of AzddMeC against L1210 and sarooma 180 cells in vitro and found that the compound, as well as 3'-azido-2',3'-dideoxycytidine (AzddC), are inactive against both cell lines. Lin, et al., reported that 3'-azido-2',3'-dideoxycytidine exhibits only marginal inhibitory activity toward two particular enzymes isolated from L1210 cells, and that AzddMeC exhibits only modest activity toward the same enzymes.

Although AzddMeC is a known compound, it has not been known that the compound had antiviral activity, especially against HIV. The discovery that delivery systems containing this compound in low concentrations exert significant activity against HIV while at the same time display low toxicity toward healthy cells represents a significant advance in antiviral research.

The compound of the present invention can be administered in the form of a pharmaceutically acceptable salt, such as a potassium, sodium, or amine salt.

Suitable methods of synthesis of 5-methyl-3'-azido-2',3'-dideoxycytidine are found in the literature and are known to those skilled in the art. See, for example: Lin, et al., J. Med. Chem. 26, 1691-1696 (1983); Horowitz, J. P., et al., J. Oro. Chem. 31, 205 (1966); Horowitz, J. P. et al., J. Org. Chem. 32, 817 (1967). Moffatt, J. G., et al. J. Org. Chem. 39, 30 (1974); and Robbins, M. et al., Tet. Letters 25, 367 (1984), all of which are incorporated herein by reference.

A specific method of synthesis of AzddMeC according the method of Lin, et al., is provided in Example 1.

EXAMPLE 1

Synthesis of 3'-azido-2',3'-dideoxy-5-methylcytidine (AzddMeC)

5'-O-Acetvl-3'-azido-3'-deoxythymidine (2)

To a pyridine (50 ml) solution of 3'-azido-3'-deoxythymidine (5.0 g, 18.7 mmole) 1 was added acetic anhydride dropwise in an ice-water bath. The mixture was allowed to stand overnight in the refrigerator. The solution was then poured into CHCl$_3$ (20 ml), washed with H$_2$O (200 ml×2), with a saturated solution of sodium bicarbonate and then H$_2$O (200 ml×2). The organic layer was then dried (MgSO$_4$). After removing the solvent, a syrup (6.5 g) was obtained.

5'-0-Acetyl-3'-azido-2',3'-dideoxy-5-methyl-4-trizolyl-1-(beta-D-ribofuranosyl) pyrimidine (3)

To a pyrimidine (60 ml) solution of compound 2 (6.5 g, 21.04 mmole) was added Cl-C$_6$H4OPOCl$_2$ (7.8 g, 31.56 mm) dropwise followed by the addition of triazole (4.35 g, 63.12 mm). The mixture was stirred at room temperature for 7 days. After stirring, methylene chloride (200 ml) was added to the reaction mixture. The resulting solution was washed with H2O (200 ml×2), saturated sodium bicarbonate solution, and then H$_2$O again. The organic layer was then dried (MgSO$_4$). Evaporation of solvent gave a yellowish solid (5.04 g).

3'-Azido-2',3'-dideoxy-5-methylcytidine (4, AzddMeC)

Compound 3 (5.04 g, 13.96 mm) was dissolved in 30 ml of ammonium hydroxide-dioxane (1:3). The reaction mixture was stirred at room temperature for 1 hour and then the solvent was evaporated to a syrup. The resulting syrup was stored in a saturated solution of ammonia in methanol at room temperature overnight. The reaction mixture was then evaporated to dryness and the residue was purified on a silica gel column using CHCl$_3$ and methanol in a 10:1 ratio and then in a 5:1 ratio as eluents. The fractions were combined and evaporated to yield AzddMeC as a solid (4, 2.9 grams).

EXAMPLE 2

Antiviral and Cytotoxic Activity of AzddMeC.

The ability of AzddMeC to inhibit HIV can be measured by various experimental techniques. The technique used herein, and described in detail below, measures the inhibition of viral replication in phytohemagglutinin (PHA) stimulated human peripheral blood mononuclear (PBM) cells infected with HIV-1 (strain LAV). The amount of virus produced is determined by measuring the virus-coded reverse transcriptase enzyme. The amount of enzyme produced is compared to an HIV control. The method is described in detail below.

Antiviral and Cytotoxic Assay in Human Peripheral Blood Mononuclear Cells. A. Three-day-old phytohemagglutinin-stimulated PBM cells ($10^6$ cells/ml) from hepatitis B and HIV1 seronegative healthy donors were infected with HIV-1 (strain LAV) at a concentration of about 100 times the 50% tissue culture infectious dose (TICD 50) per ml and cultured in the presence and absence of various concentrations of antiviral compounds.

B. Approximately 45 minutes after infection, the medium, with the compound to be tested (2 times the final concentration in medium) or without compound, was added to the flasks (5ml; final volume 10 ml). AZT was used as a positive control.

C. The cells were exposed to the virus (about $2 \times 10^5$ dpm/ml, as determined by reverse transcriptase assay) and then placed in a $CO_2$ incubator. HIV-1 (strain LAV) was obtained from the Center for Disease Control, Atlanta, Georgia. The methods used for culturing the PBM cells, harvesting the virus and determining the reverse transcriptase activity were those described by McDougal et al. (*J. Immun. Meth.* 76, 171-183, 1985) and Spira et al. (*J. Clin. Meth.* 25, 97-99, 1987), except that fungizone was not included in the medium (see Schinazi, et al., *Antimicrob. Agents Chemother.* 32, 1784-1787 (1988)). The reverse transcriptase activity in the virus-infected control was about $2 \times 10^5$ dpm per ml. Blank and uninfected cell control values were about 300 and 1,000 dpm, respectively. Similar results are obtained when Step C is performed before step B.

D. On day 6, the cells and supernatant were transferred to a 15 ml tube and centrifuged at about 900g for 10 minutes. Five ml of supernatant were removed and the virus was concentrated by centrifugation at 40,000 rpm for 30 minutes (Beckman 70.1 Ti rotor). The solubilized virus pellet was processed for determination of the levels of reverse transcriptase. Results are expressed in dpm/ml of sampled supernatant.

In vitro macrophage HIV-1 Infection Assay.

Monocytes/macrophages were isolated, as previously described Crowe S., Mills J., and McGrath, M.S., "Quantitative immunocytofluorographic analysis of DC4 surface antigen expression and HIV infection of peripheral blood monocyte/macrophages", *AIDS Res Human Retro.* 3, 135-145 (1987) from buffy coats of blood obtained from the American Red Cross, Atlanta, Ga. The cells were placed in Teflon ™ culture vessels (Savillex, Minnetonka, Minn.) in RPMI-1640 supplemented with 10% AB-positive (blood group) human serum at a density of $5 \times 10^5$ cells/ml. After 7-20 days in culture, while lymphocyte contamination is minimal, macrophages are exposed to HIV-1 (strain HIV-DV) at room temperature for one hour at a multiplicity of infection approximating one $TCID_{50}$ unit/cell. Unbound virus is removed by washing with undiluted fetal calf serum. Cells are then re-suspended and $10^5$ cells/well added to a 96 well microdilution plate in the absence or presence of various DHEA dilutions in duplicate. Nine days after acute infection, supernatants are harvested and HIV-1 p24 antigen quantitated using the Abbott HTLVIII-EIA. Percent inhibition of p24 in DHEA treated cells compared with untreated, infected control cells is calculated for all studies.

The median effective ($EC_{50}$) concentrations for various 2',3'-dideoxy- and 2',3'-dideoxydidehydronucleosides, as determined by the median effect method (*Antimicrob. Agents Chemother.* 30, 491-498 (1986), are shown in Table I. Briefly, the percent inhibition of virus, as determined from measurements of reverse transcriptase, is plotted versus the micromolar concentration of compound. The $EC_{50}$ is the concentration of compound at which there is a 50% inhibition of viral growth.

Table I also indicates the effect of compounds on the growth of uninfected human PBM cells. Mitogen-stimulated PBM cells ($3.8 \times 10^5$ cells/ml) were cultured in the presence and absence of drugs under similar conditions as those used for the antiviral assay described above. The cells were counted after 6 days using a hemacytometer and the trypan blue exclusion method, as described by Schinazi et al., *Antimicrobial Agents and Chemotherapy* 22(3), 499 (1982). The $IC_{50}$ is the concentration of compound which inhibits 50% of normal cell growth.

It has now been discovered, as shown in Table I, that the effective dose of AzddMeC in cell culture against HIV is in the range of 0.08-0.22 micromolar, while the toxic dose for host PBM or Vero cells is greater than 200 micromolar and 400 micromolar, respectively. The compound is not active against herpes simplex virus type 1 or coxsackievirus B4 and only weakly active against Friend murine retrovirus ($EC_{50}=36$ μM). Accordingly, as used herein, antiviral activity refers to the ability of a composition to inhibit the replication of HIV.

The compound is extremely active in human macrophages infected with HIV-1 ($EC_{50}=0.006$ μM), and about one hundred times less toxic to granulocyte macrophage precursor cells than AZT. More importantly, this compound exhibits no toxicity to erythroid precursor cells when tested up to 100 μM, making it one of the least toxic nucleoside analogues ever tested in this system.

FIG. 1 is a graph showing the relative effects of 3'-azido-3'-deoxythymidine (AZT), 3'-azido-2',3'-dideoxyuridine (AzddU), 3'-azido-2',3'-dideoxy-5-ethyl-uridine (AzddEU) and 3'-azido-2',3'-dideoxy-5-methyl-cytidine (AzddMeC) on colony formation of human granulocytes-macrophage precursor cells. The method used to determine the effect of varying concentrations of compound on human bone marrow progenitor cells is described in Sommadossi, Carlisle, Schinazi and Zhou, *Antimicrobial Agents and Chemotherapy* 32(7), 997 (1988). Briefly, normal human bone marrow cells were incubated at 37° C. for 2 hours with various concentrations of drug, and cells were washed twice prior to plating. Cell viability was determined by soft-agar cloning and measurement of colony formation after drug treatment.

The results reported in FIG. 1 clearly show a significant difference in the effect of AzddMeC on colony formation of human granulocytes-macrophage precursor cells in comparison to AZT. At a concentration of 10 micromolar, AzddMeC was less toxic to the cells than AzddU, which is about 20 fold less toxic to these cells than AZT. The in vitro human bone marrow is a good prognosticator of potential problems that may occur in humans administered these nucleosides. (See Sommadossi, Carlisle, *Antimicrob. Agents Chemother.* 31, 452–454 (1987).)

These data clearly demonstrate that AzddMeC (No. 20 in Table I) is a selective antiviral compound with a therapeutic index of greater than 1,000. The therapeutic index of a compound, calculated as $IC_{50}/EC_{50}$, is a measure of the margin of toxicological safety in administering an effective dose of the compound. The low toxicity of this compound could not have been predicted on the basis of chemical structure or prior knowledge in the area of antiviral research.

The discovery that AzddMeC is active against HIV at low concentrations and at the same time quite low in toxicity to normal, uninfected, host cells at the lower concentration is surprising, since a known compound of close structural similarity, AZT, exhibits a greater toxicity as measured by various experiments.

Further, 3'-azido-2',3'-dideoxy-5-methylcytidine does not substantially inhibit the replication of human bone marrow progenitor cells.

TABLE I

Anti-Viral Activity and Cytotoxicity of Nucleosides.

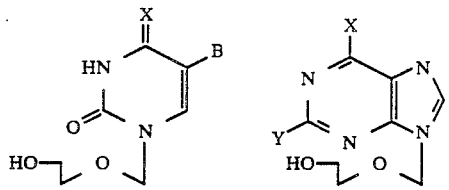

| Compound | B | X | Y | $EC_{50}$ ($\mu$M) | $IC_{50}$ ($\mu$M) |
|---|---|---|---|---|---|
| 1. 2',3'-dideoxy uridine | H | O | — | 96.8 | >100 |
| 2. 2',3'-dideoxy thymidine | CH₃ | O | — | 0.17 | >100 |
| 3. 2',3'-dideoxy-5-ethyluridine | C₂H₅ | O | — | 4.9 | >100 |
| 4. 2',3'-dideoxy cytidine | H | NH | — | 0.011 | >100 |
| 5. 2',3'-dideoxy-2'3'-didehydro uridine | H | O | — | 79.2 | >100 |
| 6. 2',3'-dideoxy-2'3'-didehydro thymidine | CH₃ | O | — | 0.009 | 70 |
| 7. 2',3'-dideoxy-2'3'-didehydro 5-ethyluridine | C₂H₅ | O | — | 75.7 | >100 |
| 8. 2',3'-dideoxy-2'3'-didehydro cytidine | H | NH | — | 0.005 | 65 |
| 9. 2',3'-dideoxy inosine | — | OH | H | 2.03 4.93 5.97 | >100 |
| 10. 2',3'-dideoxy adenosine | — | NH₂ | H | 0.91 | >100 |
| 11. 2',3'-dideoxy guanosine | — | OH | NH2 | 2.16 1.06 | >100 |
| 12. 2',3'-dideoxy-2',3'-didehydro inosine | — | OH | H | >100 | >100 |

TABLE I-continued

Anti-Viral Activity and Cytotoxicity of Nucleosides.

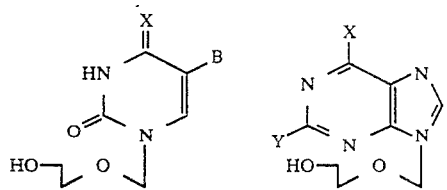

| Compound | B | X | Y | $EC_{50}$ ($\mu$M) | $IC_{50}$ ($\mu$M) |
|---|---|---|---|---|---|
| 13. 2',3'-dideoxy-2',3'-didehydro adenosine | — | NH₂ | H | 0.76 | >100 |
| 14. 2',3'-dideoxy-2',3'-didehydro N⁶-methyladenosine | — | NHCH₃ | H | 3.43 4.69 | >100 |
| 15. 2',3'-dideoxy-2',3'-didehydro guanosine | — | OH | NH₂ | >100 | >100 |
| 16. C-nucleoside of 2',3'-dideoxy cytidine | | | | >100 | >100 |
| 17. C-nucleoside of 2',3'-dideoxy-2',3'-didehydro cytidine | | | | >100 | >100 |
| 18. 3'-azido-3'-deoxythymidine (AZT) | | | | 0.002 | 200 |
| 19. 3'-azido-2,3-dideoxy-5-methyl-cytidine (AzddMeC) | | | | 0.081–0.22 | >200 |

EXAMPLE 3

Preparation of Pharmaceutical Composition.

Humans suffering from diseases caused by HIV infection can be treated by administering to the patient an effective amount of 3'-azido-2',3'-dideoxy-5-methylcytidine or its salts in the presence of a pharmaceutically acceptable carrier or diluent.

The active materials can be administered by any appropriate route, for example, orally, parenterally, intravenously, intradermally, subcutaneously, or topically, in liquid or solid form.

The active compound is included in the pharmaceutically acceptable carrier or diluent in an amount sufficient to deliver to a patient a therapeutically amount of compound to inhibit HIV replication in vivo in the absence of serious toxic effects-patient treated. By "HIV inhibitory amount" is meant an amount of active ingredient sufficient to exert an HIV inhibitory effect as measured by, for example, an assay such as the ones described herein.

These preparations should produce a serum concentration of active ingredient of from about 0.2 to 40 $\mu$M. A preferred concentration range is from 0.2 to 20 $\mu$M and most preferably about 1 to 10 $\mu$M.

The pharmaceutical compositions should provide a dosage of from 1 to 60 milligrams of compound per kilogram of body weight per day. The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

3'-Azido-2',3'-dideoxy-5-methylcytidine or its salts can be administered as a component of an elixir, suspension, syrup, wafer, chewing gum or the like. A syrup may contain, in addition to the active compounds, sucrose as a sweetening agent and certain preservatives, dyes and colorings and flavors.

3'-Azido-2',3'-dideoxy-5-methylcytidine can also be mixed with other active materials which do not impair the desired action, or with materials that supplement the desired action, such as antibiotics, antifungals, antiinflammatories, or other antivirals, including other nucleoside anti-HIV compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of 3'-azido-2',3'-dideoxy-5-methylcytidine or its monophosphate, diphosphate, and/or triphosphate derivatives are then introduced into the container. The container is then swirled by hand to free lipid material from the sides of the container and to disperse lipid aggregates, thereby forming the liposomal suspension.

EXAMPLE 4

Preparation of Phosphate Derivatives of AzddMeC

The phosphate compounds of the present invention are prepared by phosphorylation of 3'-azido-2,3-dideoxy-5-methylcytidine as described below.

The monophosphate can be prepared according to the procedure of Imai et al., *J. Org. Chem.*, 34(6), 1547–1550 (June 1969). For example, about 100 mg of AzddMeC and about 280 $\mu$l of phosphoryl chloride are reacted with stirring in about 8 ml of dry ethyl acetate at about 0° C. for about four hours. The reaction is quenched with ice. The aqueous phase is purified on an activated charcoal column, eluting with 5% ammonium hydroxide in a 1:1 mixture of ethanol and water. Evaporation of the eluant gives 100 mg of the ammonium-(3'-azido-2',3'-dideoxy-5-methylcytidine)- 5'-monophosphate.

The diphosphate can be prepared according to the procedure of Davisson et al., *J. Org. Chem.*, 52(9), 1794–1801 (1987). 3'-azido-2',3'-dideoxy-5-methylcytidine-5'-diphosphate may be prepared from the tosylate of AzddMeC, which may be prepared, for example, by reacting AzddMeC with tosyl chloride in pyridine at room temperature for about 24 hours, working up the product in the usual manner (e.g., by washing, drying, and crystallizing it).

The triphosphate can be prepared according to the procedure of Hoard et al., *J. Am. Chem. Soc.*, 87(8), 1785-1788 (1965). For example, 3'-azido-2',3'-dideoxymethylcytidine-5'-monophosphate is activated (by making a imidazolide, according to methods known to those skilled in the art) and treating with tributyl ammonium pyrophosphate in DMF. The reaction gives primarily 3'-azido-2',3'-dideoxy-5-methylcytidine -5'-triphosphate, with some unreacted monophosphate and some diphosphate. Purification by anion exchange chromatography of a DEAE column is followed by isolation of AzddMeC as the triphosphate, e.g., as the tetrasodium salt.

Structurally related analogues such as phosphorylated and acylated derivatives of AzddMeC, and C-nucleoside derivatives thereof will have similar activities at generally the same in vivo concentration ranges.

Modifications and variations of the present invention relating to compositions for the treatment of HIV which include 3'-azido-2',3'-dideoxy-5-methylcytidine, and the method of treating viral diseases which include the composition described herein, will be obvious to those skilled in the art from the foregoing detailed description of the invention. Such modifications and variations are intended to come within the scope of the appended claims.

we claim:

1. A composition comprising an effective amount to inhibit human immunodeficiency virus replication in humans of an active compound of the formula:

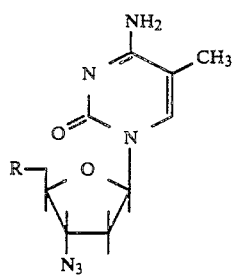

wherein R is OH, monophosphate, diphosphate, or triphosphate or a pharmacologically acceptable slat thereof in a pharmaceutically acceptable carrier, wherein the paharmaceutically acceptable carrier comprises a liposomal suspension.

2. A composition comprising an effective amount to inhibit human immunodeficiency virus replication in humans of an active compound of the formula:

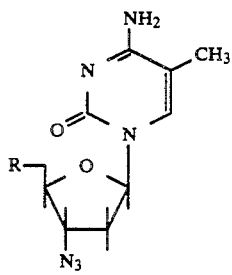

wherein R is OH, monophosphate, diphosphate, or triphosphate or a pharmacologically acceptable salt thereof in apharmaceutically acceptable carrier, wherein the pharmaceutically acceptable carrier comprises a biodegradable implant.

3. A pharmaceutical composition comprising an effective amount to inhibit human immunodeficiency virus replication in humans of a compound of the formula:

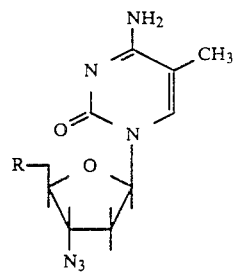

wherein R is OH, monophosphate, diphosphate, triphosphare or a pharmacologically acceptable salt thereof in a pharmaceutically acceptable carrier, and a compound selected from the group consisting of antibiotics, antifungals, antivirals, antiinflammatories, and combinations thereof.

4. A composition comprising an effective amount to inhibit human immunodeficiency virus replication in humans of an active compound of the formula:

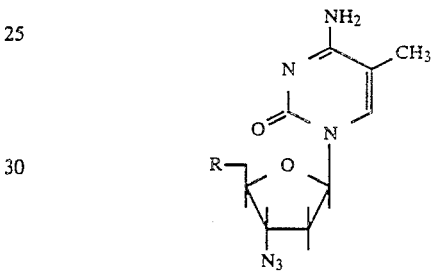

wherein R is OH, monophosphate, diphosphate, or triphosphate or a pharmacologically acceptable salt thereof in a pharmaceutically acceptable carrier, wherein the pharmaceutically acceptable carrier comprises a controlled release formulation.

5. A method for inhibiting replication of HIV in humans comprising administering an HIV inhibitory amount of a compound having the formula:

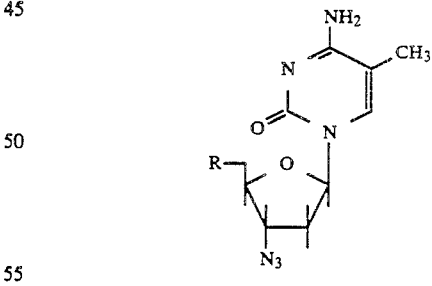

wherein R is OH, monophosphate, diphosphate, or triphosphate, or a pharmaceutically acceptable salt thereof, in association with a pharmaceutically acceptable carrier.

6. The method of claim 5, further comprising providing a material selected from the group consisting of a binder, an excipient, a disintegrating agent, a lubricant, a glidant, and an adjuvant.

7. The method of claim 5, further comprising selecting the carrier from the group consisting of oil, water, saline, buffer, polyethylene glycol, glycerine, and propylene glycol.

8. The method of claim 5 wherein the pharmaceutically acceptable carrier comprises a controlled release formulation.

9. The method of claim 5 wherein the pharmaceutically acceptable carrier comprises a liposomal suspension.

10. The method of claim 5 wherein the pharmaceutically acceptable carrier comprises a biodegradable implant.

11. The method of claim 5 further comprising administering a dosage which produces a serum concentration of compound of between approximately 0.2 and 40 $\mu$M.

12. The method of claim 5 further comprising administering a dosage which produces a serum concentration of compound of between approximately 0.2 and 20 $\mu$M.

13. The method of claim 5 further comprising administering a dosage which produces a serum concentration of compound of between approximately 1 and 10 $\mu$M.

14. The method of claim 5, further comprising providing a compound selected from the group consisting of antibiotics, antifungals, antivirals with HIV activity, antivirals without HIV activity, and antiinflammatories.

15. The method of claim 5 further comprising encapsulating the compound with a pharmaceutically acceptable carrier in an enteric coating.

* * * * *